United States Patent [19]

Visser

[11] Patent Number: 5,247,106
[45] Date of Patent: Sep. 21, 1993

[54] FATTY ACID HALIDE MANUFACTURE

[75] Inventor: Jacob B. Visser, Haastrecht, Netherlands

[73] Assignee: Unilever Patent Holdings B.V., Rotterdam, Netherlands

[21] Appl. No.: 842,259

[22] Filed: Feb. 27, 1992

[30] Foreign Application Priority Data

Feb. 27, 1991 [EP] European Pat. Off. ........... 91301584

[51] Int. Cl.$^5$ ............................................. C07C 51/00
[52] U.S. Cl. .................................... 554/159; 554/231; 562/843; 562/846
[58] Field of Search .................... 554/154, 159, 231; 562/846, 843

[56] References Cited

U.S. PATENT DOCUMENTS 2,262,431 11/1941 Ralston et al. ...................... 260/408
2,282,320 5/1942 Cahn ................................... 260/408
4,182,728 1/1980 Des Marais et al. ........... 260/544 Y

FOREIGN PATENT DOCUMENTS 1361018 7/1974 United Kingdom .

*Primary Examiner*—Jose G. Dees
*Assistant Examiner*—Deborah D. Carr
*Attorney, Agent, or Firm*—Cushman, Darby & Cushman

[57] ABSTRACT

The invention is concerned with a process for preparing a $C_6$ to $C_{24}$ fatty acid halide by reacting a fatty acid with a halogenating agent, such as phosphorus trichloride, optionally followed by hydrolysis of unreacted halogenating agent separating and removing an inorganic lower layer to leave a turbid layer containing the fatty acid chloride product. The clearing time of the turbid layer is reduced by the addition of from 3 to 20% by weight of clear fatty acid halide thereto.

9 Claims, No Drawings

FATTY ACID HALIDE MANUFACTURE

This invention relates to an improved process for the manufacture of fatty acid halides (halogenides), more in particular fatty acid chlorides. Fatty acid halogenides, in particular fatty acid chlorides are valuable commercially available compounds often used as in the manufacture of acyl taurides and certain esters and also in the manufacture of alkyl ketene dimers (AKD) used in paper sizing.

Traditionally acid chlorides have been prepared by reaction, in the liquid phase, of fatty acid with chlorinating agents like phosphorus trichloride, phosphorus pentachloride or thionylchloride followed by separation of the fatty acid halogenide obtained from the inorganic material.

It is known from DE-A- 1 280 854 (VEB Leuna-Werke "Walter Ulbricht") to react fatty acid with excess phosphorus trichloride in one or more reactors at a temperature between 40° and 80° C. and a residence time of 10 to 140 minutes and to transfer the reaction product to a separation vessel where the upper fatty acid chloride layer is separated from the lower phosphorous acid layer. The upper fatty acid chloride layer may also contain unreacted phosphorus trichloride.

When preparing fatty acid halides on a commercial scale one of the problems encountered is the separation of the fatty acid halide from the inorganic material because the settling into two layers is often difficult and time consuming inter alia because of emulsification can take place. Furthermore, once the inorganic material has separated, the fatty acid halide layer remains turbid, and may take a considerable further time to clear.

What is needed for practical scale operations is a quick separation and clarification with a clean interface before the lower inorganic layer can be removed efficiently that is within 6, preferably within 3 hours.

The invention therefore provides a method for preparing a fatty acid halide by reacting in the liquid phase a fatty acid with an inorganic halogenating agent, allowing an inorganic lower layer to separate from a turbid upper layer containing fatty acid halide and removing the lower inorganic layer, characterised in that at least 3% by weight of a clear fatty acid halide, based on the weight of the fatty acid, is added to the turbid upper layer to reduce the clearing time thereof.

We have surprisingly found that the addition of the clear fatty acid halide to the turbid upper layer is able to substantially decrease the time required for the turbid mixture to clear ("clearing time"). In practical plant scale operation, the clearing time will have a determining effect on the production capacity. Shortening of this time will evidently lead to shorter production cycles and increased capacity.

The clear fatty acid halide which is added to the turbid upper layer is preferably the halide of a $C_6$ to $C_{24}$, most preferably a $C_{14}$ to $C_{24}$ fatty acid. It may be chemically the same as that produced in the halogenation reaction. In this case, this clear fatty acid halide can be obtained by recycling or using part of the product from a previous batch. Alternatively the clear fatty acid halide which is added to the turbid upper layer may be chemically different from that produced in the halogenation reaction, in which case the final product will be a mixture of the two fatty acid halides.

European patent application no. 90313909.5 filed Dec. 19, 1990 (Unichema Chemie BV) discloses the inclusion of fatty acid amides and other fatty nitrogen compounds in the reaction mixture to improve clearing time. An advantage of the present invention is that the final product is not contaminated with such compounds and a separate purification step, to remove such compounds from the product becomes unnecessary.

British patent specification GB 1361018 (BASF) discloses the production of carboxylic acid chlorides by reacting a carboxylic acid with phosgene in the presence of dimethyl formamide. The presence of less than 0.2 mol end product is said not to adversely affect the reaction.

In accordance with the present invention the process employs a saturated or unsaturated fatty acid having at least 6 carbon atoms, such as from 6 to 24 carbon atoms, especially a $C_{14}$ to $C_{24}$, fatty acid as starting material and enables fatty halides of the same chain length to be obtained.

In a preferred embodiment of the invention the halogenating agent used is a phosphorus halide, preferably phosphorus trichloride, or pentachloride or phosgene. An alternative halogenating agent is thionyl chloride.

It is preferred that the reaction of the fatty acid with the halogenating agent is carried out in one or more reactors at a temperature between 40° and 70° C. and a residence time of 10 to 140 minutes.

The phosphorus halide is preferably used in molar excess over the fatty acid. After the reaction between fatty acid and phosphorus halide any unreacted phosphorus halide in the inorganic layer can be hydrolyzed with water to form phosphoric acid or phosphorous acid without affecting the fatty acid halide, so that a substantially pure fatty acid halide upper layer can be obtained, but this hydrolysis step is not essential. The settling of the reaction mixture into two layers is considerably facilitated according to the present invention and a clean interface is usually obtained. This invention therefore leads to a higher throughput in the existing equipment. The inorganic lower layer is then separated for example by letting the lower layer flow out of the reactor or by decanting the upper layer. A substantially pure fatty acid halide obtained.

The amount of clear fatty acid halide which is added to the turbid upper layer, preferably after the halogenation reaction has been completed, is at least 3% preferably between 5 and 50%, more preferably between 5 and 20% by weight, calculated on the basis of the amount of starting fatty acid material. Addition of the clear fatty acid halide can be made to the turbid mixture before, simultaneously with, or after the removal of the inorganic layer. The addition can be made at a temperature between 40° and 70° C., preferably at approximately the same temperature as the reaction mixture.

Addition can be made immediately after completion of the reaction, but can also be done after a first settling period of between 5 and 120 minutes. Addition can be done in the reaction tank or after transfer of the fatty acid halide to another settling tank.

EXAMPLES

In a 1 liter double-walled, three neck glass reactor, fatty acids are heated to a temperature of 70° C. with stirring. Phosphorus trichloride (0.5 mole for each 1.0 mole of fatty acid) is added dropwise over a period of 10 minutes to the fatty acid. After addition, the reaction mixture is stirred for another 15 minutes, applying a pressure of about 800 mbar (absolute). After this period the stirring is stopped and the pressure is brought back to atmospheric. The fatty acid chloride layer is now turbid and cloudy. To this layer, a certain amount of clear fatty acid chloride is added, this having been obtained from a previous experiment in which no such addition was made. This previous experiment is then also used as a reference test to determine the clearing time of the fatty acid chloride layer without addition.

The turbid fatty acid chloride layer, with the added clear fatty acid chloride was then left to clear at a temperature of 70° C. Clearance was judged visually. The time taken for clearance was taken as the clearing time. Results are given in the Table of Results below.

In Examples 1A and 1B, a "Tallow 6" based mixture of saturated fatty acids used. The added clear fatty acid chloride was obtained from the same source material and was added at a level of 5% in Example 1A and 10% in Example 1B, based on the weight of the fatty acid starting material.

In Examples 2A to 2E, "Tallow 2" based mixture of saturated fatty acids was used. Different clear fatty acid chlorides were added at a level of 10%, being based on the following fatty acids:

| Example | Fatty acid |
|---|---|
| 2A | "Tallow 2" |
| 2B | 98% lauric acid |
| 2C | 93% palmitic acid |
| 2D | 98% stearic acid |
| 2E | 98% behenic acid |

In Examples 3A and 3B, 98% lauric acid was used. Clear fatty acid chlorides (10% by weight) of lauric acid (Example 3A) and of 98% behenic acid (Example 3B) were added.

In Examples 4A to 4C, 93% palmitic acid was used. The effect of various amounts of clear fatty acid chloride (ex palmitic acid) were tested, being 3% in Example 4A, 5% in Example 4B and 10% in Example 4C.

In Example 5A, a 55/45 mixture of pure $C_{16}$ and pure $C_{18}$ fatty acids was taken. Clear fatty acids based on the same mixture were added at 10%.

TABLE OF RESULTS

| EXAMPLE | FATTY ACID | FATTY ACID HALIDE | LEVEL % | TIME (hrs) |
|---|---|---|---|---|
| 1X* | Tallow 6 | — | — | 2.90 |
| 1A | Tallow 6 | Tallow 6 | 5 | 1.00 |
| 1B | Tallow 6 | Tallow 6 | 10 | 1.00 |
| 2X* | Tallow 2 | — | — | 2.15 |
| 2A | Tallow 2 | Tallow 2 | 10 | 1.00 |
| 2B | Tallow 2 | $C_{12}$ | 10 | 2.10 |
| 2C | Tallow 2 | $C_{16}$ | 10 | 0.90 |
| 2D | Tallow 2 | $C_{18}$ | 10 | 1.00 |
| 2E | Tallow 2 | $C_{22}$ | 10 | 1.25 |
| 3X* | $C_{12}$ | — | — | >8.00 |
| 3A | $C_{12}$ | $C_{12}$ | 10 | 6.50 |
| 3B | $C_{12}$ | $C_{22}$ | 10 | 1.20 |
| 4X* | $C_{16}$ | — | — | 5.00 |
| 4A | $C_{16}$ | $C_{16}$ | 3 | 4.30 |
| 4B | $C_{16}$ | $C_{16}$ | 5 | 1.00 |
| 4C | $C_{16}$ | $C_{16}$ | 10 | 1.00 |
| 5X* | $C_{16/18}$ | — | — | 4.50 |
| 5A | $C_{16/18}$ | $C_{16/18}$ | 10 | 0.60 |

*Control experiments
Note: "Tallow 2" and "Tallow 6" based hardened fatty acids are defined in BS 3919 (1987).

I claim:

1. In a method for preparing a fatty acid halide by reacting in the liquid phase a fatty acid with an inorganic halogenating agent, allowing an inorganic lower layer to separate from a turbid upper layer containing fatty acid halide and removing the lower inorganic layer, the improvement which comprises adding at least 3% by weight of a fatty acid halide, based on the weight of the fatty acid, to the turbid upper layer to reduce the clearing time thereof.

2. A process according to claim 1 wherein the fatty acid is a saturated or unsaturated $C_6$ to $C_{24}$ fatty acid.

3. A process according to claim 1 wherein the halogenating agent is a phosphorus halide.

4. A process according to claim 3, wherein the phosphorus halide is selected from phosphorus trichloride, phosphorus pentachloride and phosgene.

5. A process according to claim 1, wherein the fatty acid halide is added to the turbid upper layer after completion of the reaction.

6. A process according to claim 1 in which from 3 to 50%, calculated on the fatty acid, is added to the turbid upper layer.

7. A process according to claim 1, characterised in that the fatty acid halide which is added to the turbid upper layer is derived from a saturated or unsaturated fatty acid having from 6 to 24 carbon atoms.

8. A process according to claim 6 wherein 5 to 20% by weight of fatty acid halide is added to facilitate clearing of the turbidity of the upper layer.

9. The method which comprises using a fatty acid halide as a clearing additive for a turbid fatty acid halide-containing liquid prepared by reacting, in a liquid phase, a fatty acid with an inorganic halogenating agent, allowing an inorganic lower layer to separate from the reaction mixture and removing the inorganic lower layer.

* * * * *